(12) United States Patent
Sawant et al.

(10) Patent No.: US 9,192,877 B2
(45) Date of Patent: Nov. 24, 2015

(54) APPARATUS AND PROCESS FOR USING A NITROALKANE AS AN ENTRAINER FOR AZEOTROPIC REMOVAL OF WATER FROM AQUEOUS ACID SOLUTION

(75) Inventors: Mahesh Ratnakar Sawant, Pune (IN); Daniel M. Trauth, Crystal Lake, IL (US); John G. Pendergast, Lake Jackson, TX (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 276 days.

(21) Appl. No.: 13/990,352

(22) PCT Filed: Dec. 7, 2011

(86) PCT No.: PCT/US2011/063692
§ 371 (c)(1),
(2), (4) Date: May 29, 2013

(87) PCT Pub. No.: WO2012/078725
PCT Pub. Date: Jun. 14, 2012

(65) Prior Publication Data
US 2013/0245340 A1  Sep. 19, 2013

Related U.S. Application Data

(60) Provisional application No. 61/421,887, filed on Dec. 10, 2010.

(51) Int. Cl.
*B01D 3/34* (2006.01)
*C07C 205/00* (2006.01)
*B01D 3/36* (2006.01)
*C07C 201/08* (2006.01)
*C07C 201/16* (2006.01)

(52) U.S. Cl.
CPC ............... *B01D 3/36* (2013.01); *C07C 201/08* (2013.01); *C07C 201/16* (2013.01)

(58) Field of Classification Search
CPC .. C07C 205/02; C07C 201/16; C07C 201/08; B01D 3/36
USPC .................................... 203/68; 568/948, 947
See application file for complete search history.

(56) References Cited

U.S. PATENT DOCUMENTS

| | | | |
|---|---|---|---|
| 1,917,391 A | 7/1933 | Othmer | |
| 2,050,234 A | 8/1936 | Othmer | |
| 3,830,707 A | 8/1974 | Kageyama et al. | |
| 4,476,336 A | 10/1984 | Sherwin | |
| 4,661,208 A | 4/1987 | Honma et al. | |
| 5,928,478 A | 7/1999 | Berg | |
| 8,410,323 B2 | 4/2013 | Sawant et al. | |
| 8,415,514 B2 | 4/2013 | Trauth | |
| 8,431,754 B2 | 4/2013 | Sawant et al. | |
| 2010/0212318 A1 | 8/2010 | Schaal | |

FOREIGN PATENT DOCUMENTS

| | | |
|---|---|---|
| CN | 101881941 | 11/2010 |
| GB | 298137 | 9/1929 |
| GB | 815091 | 6/1959 |
| JP | 6153524 | 11/1986 |
| JP | 2010190460 | 9/2010 |
| WO | WO2008128004 | 10/2008 |
| WO | WO2009013623 | 1/2009 |
| WO | WO2012078728 | 6/2012 |

OTHER PUBLICATIONS

Japanese Patent Application No. 2013-531670, Notice of Reasons for Rejection, mailed Oct. 14, 2014.
Second Office Action on Chinese Application 201180059764.2, mailed Dec. 26, 2014.
Office Action on Japanese Application 2013-542257, mailed Dec. 9, 2014 (English translation provided).
Chinese Patent Application No. 201180059764.2, Notification of First Office Action, Apr. 16, 2014.
International Application No. PCT/US2011/063692, International Search Report, mailed Mar. 2, 2012.
International Application No. PCT/US2011/063692, Written Opinion of the International Searching Authority, mailed Mar. 2, 2012.
International Application No. PCT/US2011/063692, International Preliminary Report on Patentability, mailed Jun. 20, 2013.
International Application No. PCT/US2011/063697, International Search Report, mailed Mar. 13, 2012.
International Application No. PCT/US2011/063697, Written Opinion of the International Searching Authority, mailed Mar. 13, 2012.
International Application No. PCT/US2011/063697, International Preliminary Report on Patentability, mailed Jun. 20, 2013.
Fredenslund et al., Group-Contribution Estimate of Activity Coefficients in Nonideal Liquid Mixtures, AIChE Journal, vol. 21, No. 6, Nov. 1975, pp. 1086-1099.
Japanese Patent Application No. 2013-542257, Notice of Reasons for Rejection, mailed Jul. 22, 2014.

*Primary Examiner* — Jafar Parsa

(74) *Attorney, Agent, or Firm* — Foley & Lardner LLP

(57) ABSTRACT

Disclosed are a process and an apparatus for concentrating an organic acid by using a nitroalkane as an entrainer for the azeotropic removal of water from an aqueous organic acid solution. The nitroalkane may be the same as a nitroalkane that is the product of a high pressure nitration process that produces nitroalkanes and aqueous organic acid.

20 Claims, 3 Drawing Sheets

APPARATUS AND PROCESS FOR USING A NITROALKANE AS AN ENTRAINER FOR AZEOTROPIC REMOVAL OF WATER FROM AQUEOUS ACID SOLUTION

CROSS REFERENCE TO RELATED APPLICATION

The present application claims priority to International Application No. PCT/US11/63692, filed Dec. 7, 2011, which claims priority to U.S. Provisional Patent Application No. 61/421,887 filed on Dec. 10, 2010, all of which are incorporated herein by reference in its their entireties.

FIELD

This invention relates to use of a nitroalkane as an entrainer. More specifically, this invention relates to processes and apparatuses for using a nitroalkane as an entrainer for the azeotropic removal of water from an organic acid stream produced during nitroalkane synthesis.

BACKGROUND

In a high pressure nitration process, a hydrocarbon, such as propane, and an organic acid, such as acetic acid, propanoic acid, and/or butanoic acid, reacts with aqueous nitric acid to yield products such as nitromethane, 1-nitropropane, and 2-nitropropane. In addition, the process produces a significant amount of water and some organic acids. Many of the organic acids fed to the reactor are not converted in a single pass through the reactor. Thus, in order to recycle the organic acids back to the reactor, much of the water needs to be removed. Because the relative volatility between acetic acid and water is low, conventional distillation is energy-consuming and costly. In addition, propionic and n-butanoic acid form low-boiling azeotropes with water, resulting in unavoidable acid losses in the distillation overhead if conventional distillation is used. Alkyl acetates may be used as entrainers for azeotropically removing water from an aqueous organic acid stream. However, because the recovered organic acid is recycled back to the reactor, the presence of alkyl acetates in the organic acid stream could pose potential problems. A need exists, therefore, for more economical and energy efficient processes and apparatuses for the removal of water from organic acid streams. A need also exists for processes and apparatuses to recover an organic acid stream that can be recycled for use in a high pressure nitration process without additional purification.

BRIEF SUMMARY

In one aspect, an illustrative embodiment provides a process comprising supplying a feed stream to an azeotropic distillation column, wherein the feed stream comprises water and an organic acid; and using a nitroalkane as an entrainer in the azeotropic distillation column, such that the feed stream is separated into at least a top stream and a bottom stream, wherein the top stream comprises the nitroalkane and water and wherein the bottom stream comprises the organic acid. The process further comprises separating the top stream into an organic phase and an aqueous phase, the organic phase comprising the nitroalkane; and returning at least a portion of the organic phase to the azeotropic distillation column.

In another aspect, an illustrative embodiment provides a process comprising reacting a hydrocarbon feedstock with aqueous nitric acid in a reactor to produce a product stream comprising a product nitroalkane and byproducts; degassing the product stream to produce a liquid stream; separating the liquid stream in a stripping apparatus into a first top stream and a first bottom stream, wherein the first top stream comprises the product nitroalkane and the first bottom stream comprises at least one organic acid and water; and supplying the first bottom stream to an azeotropic distillation column. The process further comprises using a working nitroalkane as an entrainer in the azeotropic distillation column, such that the first bottom stream is separated into at least a second top stream and a second bottom stream, wherein the second top stream comprises the working nitroalkane and water and wherein the second bottom stream comprises the at least one organic acid; separating the second top stream in a phase separator into an organic phase and an aqueous phase, the organic phase comprising the working nitroalkane; and returning at least a portion of the organic phase and at least a portion of the aqueous phase to the azeotropic distillation column.

In another aspect, an illustrative embodiment provides an apparatus comprising an azeotropic distillation column configured to use a nitroalkane as an entrainer to separate a feed stream into a top stream and a bottom stream, wherein the feed stream comprises water and an organic acid, wherein the top stream comprises the nitroalkane and water, and wherein the bottom stream comprises the organic acid; and a phase separator configured to separate the top stream into an organic phase and an aqueous phase, the organic phase comprising the nitroalkane.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In one aspect, a process is provided for using a nitroalkane as an entrainer in an azeotropic distillation column in order to remove water from an aqueous organic acid solution.

Figure 1:
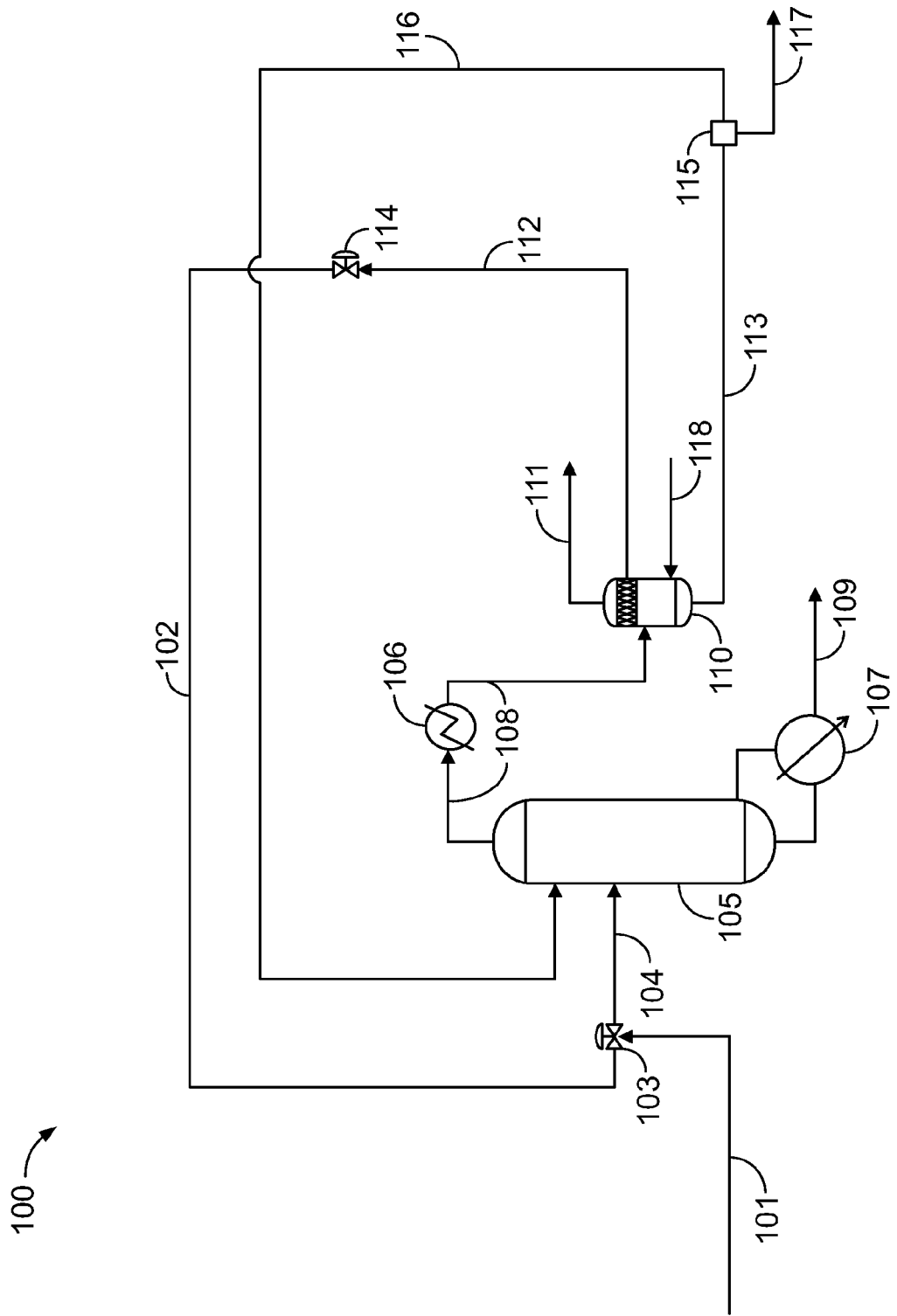
FIG. 1 is a schematic diagram of an apparatus for removing water from an organic acid solution, in accordance with an illustrative embodiment.

FIG. 1 illustrates an apparatus 100 for removing water from an aqueous organic acid solution. A first aqueous phase 101 may be combined with an organic phase 102 at a first control valve 103 to form a feed stream 104. The first aqueous phase 101 may comprise water and at least one organic acid. The organic acid may be acetic acid, propanoic acid, butanoic acid, another carboxylic acid, or any combination thereof. The organic phase 102 may comprise at least one nitroalkane. The nitroalkane may be a nitroalkane that forms a minimum boiling heterogeneous azeotrope with water, such as 1-nitropropane, 2-nitropropane, or nitromethane.

The feed stream 104 may be supplied to a distillation column 105. In alternative embodiments, the first aqueous phase 101 and the organic phase 102 may be supplied directly to the distillation column 105. The distillation column 105 may be an azeotropic distillation column. Heterogeneous azeotropic distillation columns may be used to separate mixtures of close relative volatility and also to break up azeotropes. The distillation column 105 may comprise a condenser 106 and a reboiler 107.

In the distillation column 105, the nitroalkane may be used as an entrainer, such that the feed stream 104 is separated into at least a top stream 108 and a bottom stream 109. The top stream 108 may comprise the nitroalkane and water. The bottom stream 109 may comprise the organic acid. The concentration of the organic acid may be about 70 weight percent or greater, more preferably about 80 weight percent or greater, and most preferably about 85 weight percent or greater. Further, the concentration of the organic acid may be about 98 weight percent or less, more preferably about 95 weight percent or less, and most preferably about 90 weight percent or less.

The top stream 108 may enter a phase separator 110. The phase separator 110 may be a decanter. The phase separator 110 may separate the top stream 108 into a gas phase 111, an organic phase 112, and a second aqueous phase 113. At least a portion of the organic phase 112 may pass through a second control valve 114 as the organic phase 102, which may be returned to the distillation column 104 or to the first control valve 103. The second aqueous phase 113 may be divided in a divider 115 into a recycled aqueous phase 116 and a discharged aqueous phase 117. The recycled aqueous phase 116 may be returned to the distillation column 105. The percentage of the second aqueous phase 113 that is returned to the distillation column 102 as the recycled aqueous phase 116 may be about 40 percent or greater, more preferably about 44 percent or greater, and most preferably about 45 percent or greater. Further, the percentage of the second aqueous phase 113 that is returned to the distillation column 102 as the recycled aqueous phase 116 may be about 60 percent or less, more preferably about 54 percent or less, and most preferably about 47 percent or less.

Additional entrainer may be added to the phase separator 110 through an entrainer make-up stream 118. The amount of additional entrainer may be added to balance the amount of entrainer removed or lost in the bottom stream 109 and/or the discharged aqueous phase 117.

Figure 2:
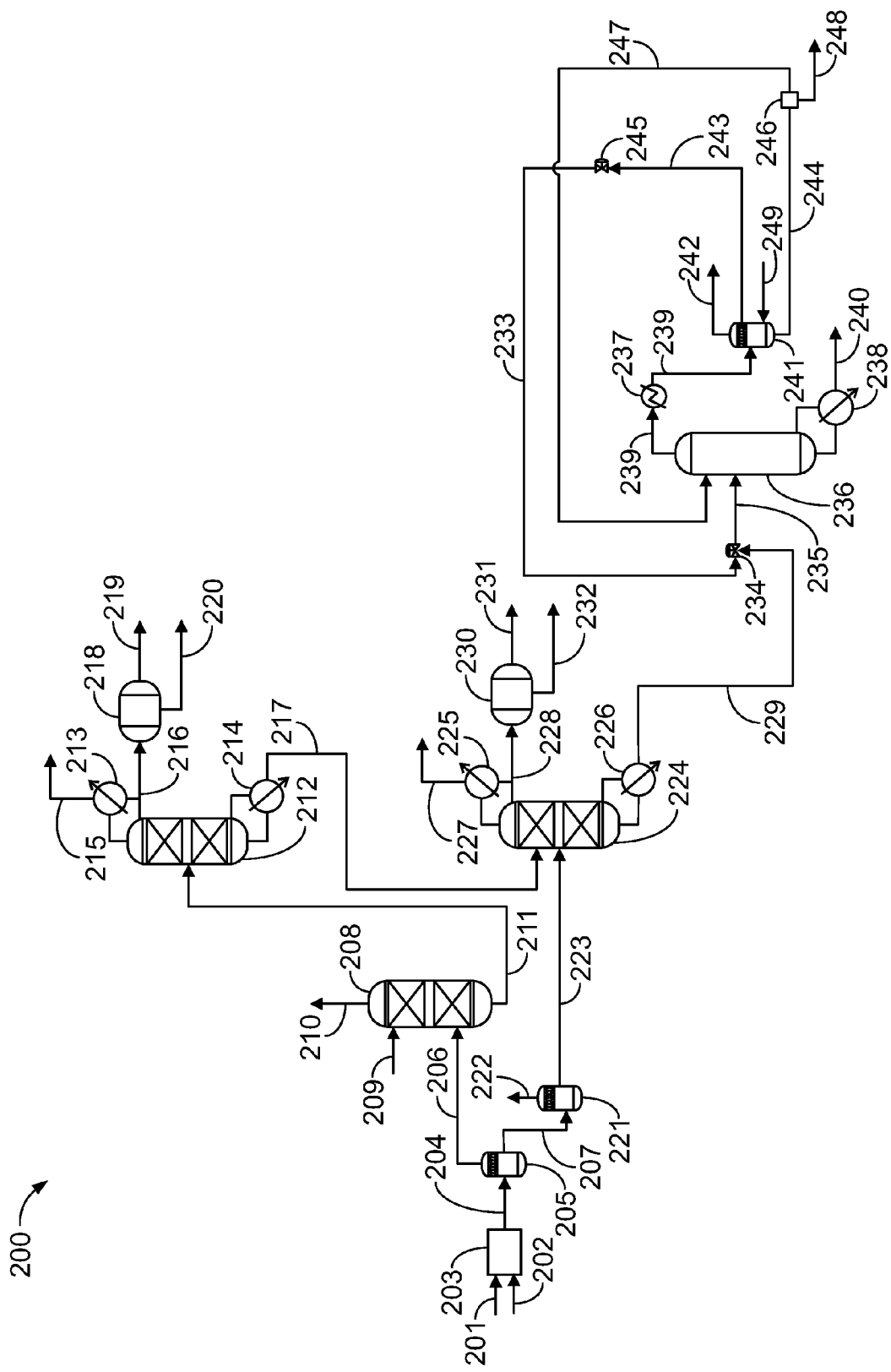
FIG. 2 is a schematic diagram of an apparatus for removing water from an organic acid solution, in accordance with an illustrative embodiment.

FIG. 2 illustrates an apparatus 200 for removing water from an aqueous organic acid solution, wherein the organic acid solution is a byproduct of a high pressure nitration process. A hydrocarbon feedstock 201 and aqueous nitric acid 202 may be introduced into a reactor 203. The hydrocarbon feedstock 201 may include, without limitation, propane, cyclohexane, isobutane, or n-octane, and an organic acid such as acetic acid, propanoic acid, butanoic acid, or hexanoic acid. The hydrocarbon feedstock 201 and the aqueous nitric acid 202 may react at a reactor pressure and a reaction temperature, such that a reaction product stream 204 comprising nitrated compounds and byproducts may be formed. The reaction product stream 204 may comprise at least one product nitroalkane. For example, when the hydrocarbon feedstock 201 comprises propane, the reaction product stream 204 may include nitropropane. When the hydrocarbon feedstock 201 comprises cyclohexane, the reaction product stream 204 may include nitrocyclohexane. When the hydrocarbon feedstock 201 comprises isobutane, the reaction product stream 204 may include tert-nitrobutane. When the hydrocarbon feedstock 201 comprises n-octane, the reaction product stream may include nitro-n-octane.

The hydrocarbon feedstock 201 and the aqueous nitric acid 202 may be mixed, or partially mixed, prior to entry into the reactor 203, or alternatively; they may be added individually, with mixing to occur within the reactor 203. In addition, the hydrocarbon feedstock 201 and the aqueous nitric acid 202, whether added together or individually, may be preheated prior to entry into the reactor 203.

The aqueous nitric acid 202 may be delivered to the reactor 203 in the form of an aqueous solution that contains at least about 10 weight percent, more preferably at least about 15 weight percent, most preferably at least about 20 weight percent, of the acid. Further, the solution may contain less than about 50 weight percent, more preferably less than about 40 weight percent, and most preferably less than about 35 weight percent, of the acid. In other embodiments, the nitric acid solution may contain between about 15 and about 40 weight percent of the acid. In further embodiments, the nitric acid solution may contain between about 18 and about 35 weight of the acid.

The mole ratio of the hydrocarbon feedstock 201 to the aqueous nitric acid 202 may be at least about 0.3:1, more preferably at least about 0.5:1.

The reactor pressure may be at least about $3.4 \times 10^6$ Pascal (500 psi), more preferably at least about $6.8 \times 10^6$ Pascal (1000 psi), and most preferably at least about $8.3 \times 10^6$ Pascal (1200 psi). In some embodiments, the pressure may be about $11.0 \times 10^6$ Pascal (1600 psi) or less, more preferably about $10.3 \times 10^6$ Pascal (1500 psi) or less, most preferably about $9.7 \times 10^6$ Pascal (1400 psi) or less. In other embodiments, the pressure may between about $6.8 \times 10^6$ Pascal (1000 psi) and $9.7 \times 10^6$ Pascal (1400 psi). Various methods known in the art may be used for maintaining the pressure within the desired range including, for example, through the use of a back-pressure regulator.

The reaction temperature within the reactor may be controlled (for example with heat exchange fluid or using heat generated from the reaction) to at least about 140 degrees Celsius and to less than about 325 degrees Celsius. In other embodiments, the temperature may be at least about 215 degrees Celsius and to less than about 325 degrees Celsius. In some embodiments, the temperature may be at least about 180 degrees, at least about 200 degrees, at least about 230 degrees, or at least about 240 degrees. In other embodiments, the temperature may be less than about 290 degrees, less than about 280 degrees, less than about 270 degrees, or less than about 250 degrees. In further embodiments, the temperature may be between about 200 and 250 degrees Celsius. In yet further embodiments, the temperature may be between about 215 and 280 degrees Celsius, or between about 220 and 270 degrees Celsius.

The residence time of the reactants in the reactor 103 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 203 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

The reactor 203 may also be packed with a packing material to improve reactant mixing and heat transfer and/or to vary the reactor volume. Packing of the reactor may be preferred, for example, in a propane nitration system where it is desired to increase the concentration of 2,2-dinitropropane in the reaction product stream. Suitable packing materials may include, for example, glass beads, random packing, or structured packing, such as those typically employed in distillation devices. Other packing materials are known in the art and may be used. The reactor 203 may also be an un-packed reactor.

The reaction product stream 204 then may enter a first degasser 205. The first degasser 205 may separate the reaction product stream 204 into a first gas phase 206 and a first liquid phase 207. The first gas phase 206 may be sent to an absorber 208. The absorber 208 may use a recycled water stream 209 to absorb any nitroalkanes in the first gas phase 206, such that a second gas phase 210 and a second liquid phase 211 are formed. In an illustrative embodiment, the recycled water in the recycled water stream 209 may be recycled from a downstream nitroalkane recovery process.

The second liquid phase 211 may be sent to a first stripping apparatus 212 in order to recover the least one product nitroalkane. The first stripping apparatus 212 may comprise a first condenser 213 and a first reboiler 214. The first stripping apparatus 212 may strip oil-soluble components from the second liquid phase 211, such that a second gas phase 215, a first oil phase 216, and a first aqueous phase 217 are formed. The first oil phase 216 may be sent to a first separator 218. The first separator 218 may be, for example, a conventional distillation column. The first separator 218 may separate the first oil phase 218 into at least a second oil phase 219 and a second aqueous phase 220. The second oil phase 219 may comprise the at least one product nitroalkane.

The first liquid phase 207 from the first degasser 205 may then enter a second degasser 221. The second degasser 221 may phase separate the first liquid phase 207 into a third gas phase 222 and a third liquid phase 223. In some illustrative embodiments, the high concentration of acetic acid may co-solubilize the nitroalkane products such that a single liquid phase 223, results rather than an oil phase and an aqueous phase. The liquid phase 223 may comprise the at least one product nitroalkane and at least one organic acid.

The liquid phase 223 may then be sent to a second stripping apparatus 224. The second stripping apparatus 224 may comprise a second condenser 225 and a second reboiler 226. The second stripping apparatus 224 may strip oil-soluble components from the third liquid phase 223, such that a fourth gas phase 227, a third oil phase 228, and a third aqueous phase 229 are formed. The third oil phase 228 may be sent to a second separator 230. The second separator 230 may be, for example, a conventional distillation column. The second separator 230 may separate the third oil phase 228 into at least a fourth oil phase 231 and a fourth aqueous phase 232. The third oil phase 231 may comprise the at least one product nitroalkane.

The third aqueous phase 229 may comprise water and at least one organic acid. The organic acid may be acetic acid, propanoic acid, butanoic acid, another carboxylic acid, or any combination thereof. The third aqueous phase 229 may be combined with an organic phase 233 at a first control valve 234 to form a feed stream 235. The organic stream 233 may comprise at least one working nitroalkane. The working nitroalkane may be a nitroalkane that forms a minimum boiling heterogeneous azeotrope with water, such as 1-nitropropane, 2-nitropropane, or nitromethane. The working nitroalkane may be the same type of nitroalkane as the at least one product nitroalkane.

The feed stream 235 may be sent to a distillation column 236, such as a heterogeneous azeotropic distillation column. Heterogeneous azeotropic distillation columns may be used to separate mixtures of close relative volatility and also to break up azeotropes. The distillation column 236 may comprise a third condenser 237 and a third reboiler 238. In the distillation column 236, the working nitroalkane may be used as an entrainer, such that the feed stream 235 is separated into at least a top stream 239 and a bottom stream 240. The top stream 239 may comprise the working nitroalkane and water. The bottom stream 240 may comprise the organic acid. The concentration of the organic acid may be about 70 weight percent or greater, more preferably about 80 weight percent or greater, and most preferably about 85 weight percent or greater. Further, the concentration of the organic acid may be about 98 weight percent or less, more preferably about 95 weight percent or less, and most preferably about 90 weight percent or less. The bottom stream 240 may be returned to the reactor 203 as an organic acid diluent in the hydrocarbon feedstock 201. In alternative embodiments, the bottom stream 240 may be used for other purposes, such as in other processes.

The top stream 239 may enter a phase separator 241. The phase separator 241 may be a decanter. The phase separator 241 may separate the top stream 229 into a fifth gas phase 242, an organic phase 243, and a fourth aqueous phase 244. At least a portion of the organic phase 244 may pass through a second control valve 245 as the organic phase 233, which may be returned to the distillation column 236 or to the first control valve 234. The fourth aqueous phase 244 may be divided in a divider 246 into a recycled aqueous phase 247 and a discharged aqueous phase 248. The recycled aqueous phase 247 may be returned to the distillation column 236. The percentage of the fourth aqueous phase 244 that is returned to the distillation column 236 as the recycled aqueous phase 247 may be about 40 percent or greater, more preferably about 44 percent or greater, and most preferably about 45 percent or greater. Further, the percentage of the fourth aqueous phase 244 that is returned to the distillation column 236 as the recycled aqueous phase 247 may be about 60 percent or less, more preferably about 54 percent or less, and most preferably about 47 percent or less.

Additional entrainer may be added to the phase separator 241 through an entrainer make-up stream 249. The amount of additional entrainer may be added to balance the amount of entrainer removed or lost in the bottom stream 240 and/or the discharged aqueous phase 248.

EXAMPLES

Various examples are demonstrated using ASPEN computer-aided process simulation software (Aspen Technology, Incorporated, Burlington, Mass.), which uses a database of measured physical properties for engineering design calculations.

Example 1

Removal of Water from Acetic Acid Using Conventional Distillation

In a high pressure nitration process, propane, nitric acid, and acetic acid react in a reactor to produce a product stream comprising nitroalkanes (nitromethane, 1-nitropropane, 2-nitropropane, 2,2-dinitropropane, nitroethane) and oxidation byproducts (acetic acid, propionic acid). The product stream also contains off-gases, such as nitrous oxide, nitric oxide, carbon dioxide, carbon monoxide, unconverted propane and water. The composition of the product stream is shown in Table 1 below.

TABLE 1

Composition of product stream of high pressure nitration process

| Chemical | Molecular Weight | kg/h (lbs/h) |
|---|---|---|
| Water | 18.0 | 14671 (32343) |
| Nitric Acid | 63.0 | 0 (0) |
| Acetic Acid | 60.1 | 20100 (44314) |
| Sodium Nitrate | 85.0 | 0 (0) |
| Propane | 44.1 | 4362 (9616) |
| Acetone | 58.1 | 308 (679) |
| Nitromethane | 61.0 | 1207 (2662) |
| Nitroethane | 75.1 | 50 (111) |
| 2-nitropropane | 89.1 | 4436 (9779) |
| 1-nitropropane | 89.1 | 606 (1336) |
| 2,2-dinitropropane | 134.1 | 64 (142) |
| Carbon dioxide | 44.0 | 2664 (5806) |
| Nitrogen dioxide | 46.0 | 0 (0) |
| Nitrous oxide | 44.0 | 514 (1133) |
| Nitric oxide | 30.0 | 2054 (4529) |
| Nitrogen | 28.0 | 338 (746) |
| Carbon monoxide | 28.0 | 499 (1101) |

The product stream is degassed in two successive degassers. The gas stream from the first degasser is then separated in an absorber (scrubbed with recycled water, for example, water from a step in the downstream nitroalkane recovery process) such that a gaseous phase and an aqueous phase are formed. The aqueous phase from the absorber is sent to a first stripping apparatus, where a small amount of recovered nitroparaffins are removed. The aqueous phase from the second degasser and the aqueous phase from the first stripping apparatus are sent to a second stripping apparatus. There, the nitroalkanes are stripped from the aqueous phases, so that the bottoms from the stripping apparatus comprise water and dissolved organic acids. The bottoms from the second stripping apparatus typically contain around 60 weight percent acetic acid which is typically concentrated to about 90 weight percent acetic acid before being recycled back to the reactor as an acetic acid diluent.

Acetic acid and water do not form an azeotrope, but are close-boiling and are often termed "near azeotropes" because the binary pair has a relative volatility that approaches one. The concentration of acetic acid from an aqueous solution by conventional distillation, therefore, is a rather difficult separation. In this process arrangement shown above, a drying column concentrates acetic acid from 60 weight percent to 90 weight percent. The drying column is designed at process specification of 98.5 percent recovery of acetic acid and 90 weight percent final purity of acetic acid in the bottoms. For 40 equilibrium stages, the drying column requires a reboiler duty of about 3,142,426 J/kg (1351 Btu/lb) feed, which is significant for a diluent concentration step.

Example 2

Heterogeneous Azeotropic Distillation Scheme for Concentrating Acetic Acid Using Nitroalkanes As in Example 1, propane, nitric acid, and acetic acid react in a reactor to produce a product stream comprising nitroalkanes (nitromethane, 1-nitropropane, 2-nitropropane, 2,2-dinitropropane, nitroethane) and oxidation byproducts (acetic acid, propionic acid). The product stream also contains off-gases, such as nitrous oxide, nitric oxide, carbon dioxide, carbon monoxide, unconverted propane and water. The composition of the product stream is shown in Table 1 above.

The product stream is degassed in two successive degassers. The gas stream from the first degasser is then separated in an absorber (scrubbed with recycled water, for example, water from a step in the downstream nitroalkane recovery process) such that a gaseous phase and an aqueous phase are formed. The aqueous phase from the absorber is sent to a first stripping apparatus, where a small amount of recovered nitroparaffins are removed. The aqueous phase from the second degasser and the aqueous phase from the first stripping apparatus are sent to a second stripping apparatus. There, the nitroalkanes are stripped from the aqueous phases, so that the bottoms from the stripping apparatus comprise water and dissolved organic acids. The bottoms from the second stripping apparatus typically comprise around 60 weight percent acetic acid which is typically concentrated to about 90 weight percent acetic acid before being recycled back to the reactor as an acetic acid diluent.

Some nitroalkanes, such as nitromethane, 2-nitropropane, and 1-nitropropane, form minimum boiling heterogeneous azeotropes with water. Therefore, a heterogeneous azeotropic distillation (HAD) column can be designed to obtain a concentrated acetic acid product at the column bottom while obtaining minimum-boiling entrainer-water azeotrope at the top of the column. The bottoms from the stripping apparatus, comprising an about 60 weight percent acetic acid solution, are mixed with a nitroalkane and supplied to the HAD column.

Table 2 below shows the azeotropic compositions of industrially practiced entrainers (e.g., alkyl acetates) and the novel proposed nitroalkane entrainers for drying aqueous acetic acid. The entrainer to feed ratio is inversely proportional to the mass percent water in the azeotropic composition. Thus, amongst alkyl acetates, the amount of entrainer required decreases with increasing carbon chain length. Correspondingly for nitroalkanes, 1-nitropropane requires the lowest entrainer to feed ratio followed by 2-nitropropane and then nitromethane.

TABLE 2

Entrainers for water-acetic acid separation

| | Azeotropic Data | | |
|---|---|---|---|
| Entrainer | Weight percent water | Temperature, degrees Celsius | Boiling Point, degrees Celsius |
| Ethyl acetate | 8 | 70.5 | 77.0 |
| n-propyl acetate | 14 | 82.8 | 101.5 |
| iso-butyl acetate | 16 | 87.7 | 116.4 |
| n-butyl acetate | 27 | 90.6 | 126.0 |
| Nitromethane | 23.6 | 83.6 | 101.2 |
| 2-nitropropane | 29.4 | 88.6 | 120.4 |
| 1-nitropropane | 36.5 | 91.6 | 131.7 |

A HAD column using 1-nitropropane as entrainer is designed to obtain the desired purity acetic acid product at the column bottom, while obtaining minimum boiling 1-nitropropane/water azeotrope at the top of the column. The 1-nitropropane/water azeotrope is heterogeneous and therefore the top column vapor stream forms two liquid phases, an organic phase and an aqueous phase, after condensation in a decanter. The organic phase comprises mostly 1-nitropropane and the aqueous phase comprises mostly water (an acid free aqueous stream (AFAS)). The entire organic phase is refluxed back towards the HAD column to provide enough 1-nitropropane to act as an entrainer. It is then mixed with the feed stream and co-fed to the HAD column. The aqueous phase is drawn out from the system for further treatment or discharge. A portion of the aqueous phase may be refluxed back to the column if the organic reflux falls short of fulfilling the column specifications.

The design basis for the HAD column using 1-nitropropane as entrainer is shown in Table 3. The optimum design and operating condition for the HAD column is obtained by performing a sensitivity analysis around the key design variables: the number of stages in the HAD column, the feed tray location, the entrainer to feed ratio, and the fraction of the decanter aqueous phase recycled. The design specifications affected by these variable changes are: reboiler duty, overall water removal, the amount of acid in the acid free aqueous stream (AFAS), and the amount of entrainer in AFAS.

TABLE 3

Design basis for 1-nitropropane based HAD column

| Operating Pressure | 101,325 Pascal (1 atm) |
|---|---|
| Flows kg/h (lb/h) | Feed |
| Acetic acid | 19891 (43853) |
| 1-nitropropane | 12 (26) |
| Water | 13185 (29068) |
| Percent acid recovery | >98% |
| Weight percent in bottoms | ~90% |

Table 4 below shows the sensitivity of the key performance specifications of the HAD column with respect to the number of equilibrium contacting stages while maintaining other variables constant. At equilibrium stages below 40, the bottom stream progressively becomes diluted with water and 1-nitropropane due to the corresponding reduction in stripping section. Increasing the stages beyond 40 effects marginal improvement in the performance specifications of the column.

TABLE 4

Sensitivity of column performance to total no. of stages

| No. of stages (stripping stages) | Feed stage | 1-NP/feed ratio | Percent of aqueous stream as reflux | Acetic acid kg/h (lb/h) AFAS | Bottoms | Water kg/h (lb/h) AFAS | Bottoms | 1-NP kg/h (lb/h) AFAS | Bottoms | Reboiler duty J/kg (Btu/lb) feed | Percent acid recovery | Weight percent acid bottoms |
|---|---|---|---|---|---|---|---|---|---|---|---|---|
| 45 (17) | 28 | 0.891 | 46% | 293 (646) | 19598 (43207) | 10963 (24169) | 2223 (4900) | 177 (391) | 9.03 × 10⁻⁶ (1.99 × 10⁻⁵) | 2.09 × 10⁶ (897.25) | 98.50 | 89.81 |
| 40 (12) | 28 | 0.891 | 46% | 293 (647) | 19598 (43207) | 10894 (24017) | 2290 (5049) | 177 (390) | 1.05 × 10⁻² (2.32 × 10⁻²) | 2.08 × 10⁶ (892.53) | 98.50 | 89.54 |
| 35 (7) | 28 | 0.891 | 46% | 294 (648) | 19597 (43205) | 10567 (23296) | 2618 (5772) | 175 (386) | 10.17 (22.43) | 2.01 × 10⁶ (868.36) | 98.50 | 88.22 |
| 30 (2) | 28 | 0.891 | 46% | 294 (649) | 19597 (43204) | 8753 (19296) | 4433 (9773) | 171 (378) | 2526.60 (5570.19) | 1.63 × 10⁶ (701.68) | 98.50 | 81.55 |

Figure 3:
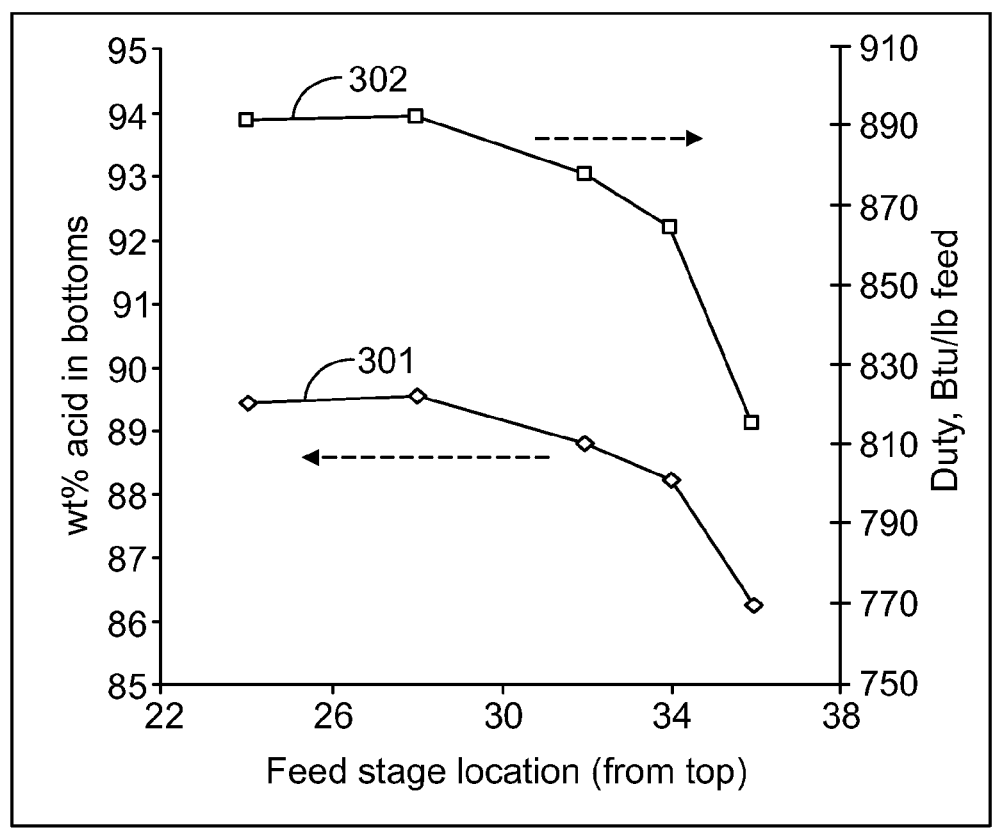
FIG. 3 is a graph of the weight percent of acetic acid in the azeotropic distillation column bottoms and the reboiler duty as a function of feed stage location.

Table 5 shows the sensitivity of key performance specifications of the HAD column with respect to the feed stage while maintaining other variables constant. As the feed stage shifts towards the reboiler, both 1-nitropropane and water start appearing in the column bottoms as shown in FIG. 3. Line 301 illustrates the decrease of weight percent acetic acid (and thus the increase of water and 1-nitropropane) in the bottoms as the feed stage approaches the reboiler. Line 302 illustrates the effect of the feed stage location on the reboiler duty (Btu/lb feed).

TABLE 5

Sensitivity of column performance to feed stage

| No. of stages (stripping stages) | Feed stage | 1-NP/feed ratio | Percent of aqueous stream as reflux | Acetic acid kg/h (lb/h) AFAS | Acetic acid kg/h (lb/h) Bottoms | Water kg/h (lb/h) AFAS | Water kg/h (lb/h) Bottoms | 1-NP kg/h (lb/h) AFAS | 1-NP kg/h (lb/h) Bottoms | Reboiler duty J/kg (Btu/lb) feed | Percent acid recovery | Weight percent acid bottoms |
|---|---|---|---|---|---|---|---|---|---|---|---|---|
| 40 | 36 | 0.891 | 46% | 298 (657) | 19593 (43196) | 10048 (22153) | 3137 (6916) | 181 (400) | 402.48 (887.32) | 1.90 × 10$^6$ (815.32) | 98.48 | 86.20 |
| 40 | 34 | 0.891 | 46% | 296 (652) | 19596 (43201) | 10559 (23278) | 2626 (5789) | 177 (390) | 39.34 (86.73) | 2.01 × 10$^6$ (864.65) | 98.49 | 88.18 |
| 40 | 32 | 0.891 | 46% | 295 (650) | 19597 (43203) | 10708 (23608) | 2476 (5459) | 176 (389) | 2.68 (5.90) | 2.04 × 10$^6$ (877.73) | 98.50 | 88.78 |
| 40 | 28 | 0.891 | 46% | 293 (647) | 19598 (43207) | 10894 (24017) | 2290 (5049) | 177 (390) | 0.01 (0.02) | 2.08 × 10$^6$ (892.53) | 98.50 | 89.54 |
| 40 | 24 | 0.891 | 46% | 292 (643) | 19600 (43210) | 10865 (23953) | 2319 (5113) | 176 (387) | 0.00 (0.00) | 2.08 × 10$^6$ (892.15) | 98.51 | 89.42 |

Figure 4:
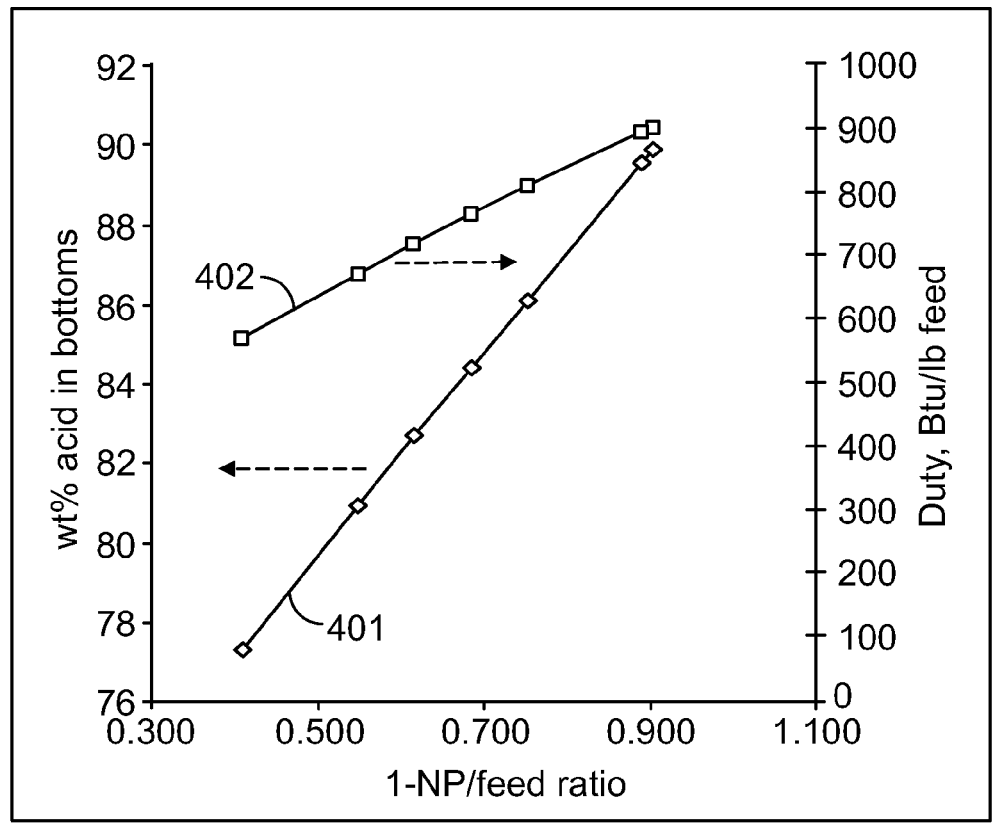
FIG. 4 is a graph of the weight percent of acetic acid in the azeotropic distillation column bottoms and the reboiler duty as a function of the 1-nitropropane/feed ratio.

The sensitivity of the HAD column performance specifications with respect to the entrainer/feed ratio while maintaining other variables constant is shown in Table 6 below and FIG. 4. The acetic acid-water separation, and therefore the reboiler duty, is highly sensitive to the 1-nitropropane/feed ratio. As shown in FIG. 4, as the 1-nitropropane flow approaches zero, the system shifts towards conventional distillation (more acetic acid in the AFAS overhead stream and more water in the bottoms). Line 401 shows the sensitivity of the weight percent acid in the bottoms with respect to the 1-nitropropane/feed ratio. Line 402 shows the sensitivity of the reboiler duty (Btu/lb feed) with respect to the 1-nitropropane/feed ratio.

The sensitivity of the HAD column performance specifications with respect to the entrainer/feed ratio while maintaining other variables constant is shown in Table 7 below. The separation of water and acetic acid is highly sensitive to aqueous phase reflux, with the separation improving at higher reflux. However, a higher aqueous phase reflux also increases the reboiler duty. Since the desired level of acid concentration in water bottoms is about 90 weight percent acetic acid, a 46 percent aqueous reflux is optimum for present purposes. Thus, the optimized operating conditions of the HAD column that satisfy the desired performance criterion are shown in Table 8 below. The HAD column requires about 34 percent less energy than conventional distillation for the same degree of separation. In addition, because 1-nitropropane is a prod-

TABLE 6

Sensitivity of column performance to 1-NP/feed ratio

| No. of stages (stripping stages) | Feed stage | 1-NP/feed ratio | Percent of aqueous stream as reflux | Acetic acid kg/h (lb/h) AFAS | Acetic acid kg/h (lb/h) Bottoms | Water kg/h (lb/h) AFAS | Water kg/h (lb/h) Bottoms | 1-NP kg/h (lb/h) AFAS | 1-NP kg/h (lb/h) Bottoms | Reboiler duty J/kg (Btu/lb) feed | Percent acid recovery | Weight percent acid bottoms |
|---|---|---|---|---|---|---|---|---|---|---|---|---|
| 40 | 28 | 0.905 | 46% | 292 (644) | 19599 (43209) | 10974 (24193) | 2211 (4874) | 178 (393) | 0.01 (0.02) | 2.09 × 10$^6$ (900.28) | 98.51 | 89.86 |
| 40 | 28 | 0.891 | 46% | 293 (647) | 19598 (43207) | 10894 (24017) | 2290 (5049) | 177 (390) | 0.01 (0.02) | 2.08 × 10$^6$ (892.53) | 98.50 | 89.54 |
| 40 | 28 | 0.754 | 46% | 306 (674) | 19586 (43179) | 10022 (22095) | 3162 (6971) | 161 (355) | 0.005 (0.01) | 1.88 × 10$^6$ (807.99) | 98.44 | 86.10 |
| 40 | 28 | 0.685 | 46% | 314 (692) | 19578 (43161) | 9561 (21078) | 3624 (7990) | 152 (336) | 0.005 (0.01) | 1.78 × 10$^6$ (764.00) | 98.40 | 84.38 |
| 40 | 28 | 0.617 | 46% | 323 (712) | 19568 (43141) | 9075 (20007) | 4109 (9058) | 144 (317) | 0.005 (0.01) | 1.67 × 10$^6$ (718.39) | 98.35 | 82.65 |
| 40 | 28 | 0.548 | 46% | 334 (736) | 19558 (43117) | 8566 (18884) | 4619 (10183) | 135 (298) | 0.005 (0.01) | 1.56 × 10$^6$ (671.17) | 98.29 | 80.89 |
| 40 | 28 | 0.411 | 46% | 360 (794) | 19531 (43059) | 7445 (16413) | 5740 (12655) | 116 (255) | 0.005 (0.01) | 1.33 × 10$^6$ (570.02) | 98.16 | 77.29 | uct in the high pressure nitration process, its use avoids potential downstream purity and upstream reactor issues.

TABLE 7

Sensitivity of column performance to aqueous phase reflux

| No. of stages (stripping stages) | Feed stage | 1-NP/feed ratio | Percent of aqueous stream as reflux | Acetic acid kg/h (lb/h) | | Water kg/h (lb/h) | | 1-NP kg/h (lb/h) | | Reboiler duty J/kg (Btu/lb) feed | Percent acid recovery | Weight percent acid bottoms |
|---|---|---|---|---|---|---|---|---|---|---|---|---|
| | | | | AFAS | Bottoms | AFAS | Bottoms | AFAS | Bottoms | | | |
| 40 | 28 | 0.891 | 46% | 293 (647) | 19598 (43207) | 10894 (24017) | 2290 (5049) | 177 (390) | 0.01 (0.02) | $2.08 \times 10^6$ (892.53) | 98.50 | 89.54 |
| 40 | 28 | 0.891 | 50% | 290 (640) | 19601 (43213) | 11441 (25223) | 1744 (3845) | 186 (409) | 0.01 (0.02) | $2.27 \times 10^6$ (977.47) | 98.52 | 91.83 |
| 40 | 28 | 0.891 | 54% | 288 (636) | 19603 (43217) | 12159 (26807) | 1025 (2260) | 288 (636) | 0.01 (0.02) | $2.53 \times 10^6$ (1088.48) | 98.53 | 95.03 |

TABLE 8

Optimized operating conditions of the HAD column

| No. of stages (stripping stages) | Feed stage | 1-NP/feed ratio | Percent of aqueous stream as reflux | Acetic acid kg/h (lb/h) | | Water kg/h (lb/h) | | 1-NP kg/h (lb/h) | | Reboiler duty (J/kg) Btu/lb | Percent acid recovery | Weight percent acid bottoms |
|---|---|---|---|---|---|---|---|---|---|---|---|---|
| | | | | AFAS | Bottoms | AFAS | Bottoms | AFAS | Bottoms | | | |
| 40 | 28 | 0.891 | 46% | 293 (647) | 19598 (43207) | 10894 (24017) | 2290 (5049) | 177 (390) | 0.01 (0.02) | $2.08 \times 10^6$ (892.53) | 98.50 | 89.54 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process comprising:
   supplying a feed stream to an azeotropic distillation column, wherein the feed stream comprises water and an organic acid;
   using a nitroalkane as an entrainer in the azeotropic distillation column, such that the feed stream is separated into at least a top stream and a bottom stream, wherein the top stream comprises the nitroalkane and water and wherein the bottom stream comprises the organic acid;
   separating the top stream into an organic phase and an aqueous phase, the organic phase comprising the nitroalkane; and
   returning at least a portion of the organic phase to the azeotropic distillation column.

2. A process according to claim 1, wherein the nitroalkane is selected from the group consisting of 1-nitropropane and 2-nitropropane.

3. A process according to claim 1, wherein the bottom stream is at least 90 weight percent of the organic acid.

4. A process according to claim 1, wherein the azeotropic distillation column comprises at least forty stages.

5. A process according to claim 1, wherein the organic acid is present in the bottom stream in a higher concentration than in the feed stream.

6. A process according to claim 1, further comprising returning at least a portion of the aqueous phase to the azeotropic distillation column.

7. A process comprising:
   reacting a hydrocarbon feedstock with aqueous nitric acid in a reactor to produce a product stream comprising a product nitroalkane and byproducts;
   degassing the product stream to produce a liquid stream;
   separating the liquid stream in a stripping apparatus into a first top stream and a first bottom stream, wherein the first top stream comprises the product nitroalkane and the first bottom stream comprises at least one organic acid and water;
   supplying the first bottom stream to an azeotropic distillation column;
   using a working nitroalkane as an entrainer in the azeotropic distillation column, such that the first bottom stream is separated into at least a second top stream and a second bottom stream, wherein the second top stream comprises the working nitroalkane and water and wherein the second bottom stream comprises the at least one organic acid;
   separating the second top stream in a phase separator into an organic phase and an aqueous phase, the organic phase comprising the working nitroalkane; and
   returning at least a portion of the organic phase and at least a portion of the aqueous phase to the azeotropic distillation column.

8. A process according to claim 7, wherein the at least one organic acid is selected from the group consisting of acetic acid, propanoic acid, butanoic acid, and any combination thereof.

9. A process according to claim 7, wherein the working nitroalkane is selected from the group 1-nitropropane.

10. A process according to claim 7, wherein the product nitroalkane is selected from the group consisting of 1-nitropropane, 2-nitropropane, and nitromethane.

11. A process according to claim 7, further comprising returning at least a portion of the second bottom stream to the reactor.

12. A process according to claim 1, wherein the organic acid is selected from the group consisting of acetic acid, propanoic acid, butanoic acid, and any combination thereof.

13. A process according to claim 1, wherein the organic acid is acetic acid.

14. A process according to claim 1, wherein the azeotropic distillation operates at a pressure of about 1 atm.

15. A process according to claim 7, wherein the at least one organic acid is acetic acid.

16. A process according to claim 7, wherein the reactor is at a pressure of at least about $3.4 \times 10^6$ Pa.

17. A process according to claim 7, wherein the reactor is at a pressure range of about $6.8 \times 10^6$ Pa to about $9.7 \times 10^6$ Pa.

18. A process according to claim 7, wherein the reactor is at a temperature range of about 140° C. to about 325° C.

19. A process according to claim 7, wherein the azeotropic distillation operates at a pressure of about 1 atm.

20. A process according to claim 7, wherein the second bottom stream comprises about 70 wt % or greater of the organic acid.

* * * * *